(12) United States Patent
Aslam

(10) Patent No.: US 10,398,352 B2
(45) Date of Patent: Sep. 3, 2019

(54) INHALER SPACER WITH A MEDICAMENT COMPLIANCE SYSTEM

(71) Applicant: CLIN-E-CAL LIMITED, Stockport, Cheshire (GB)

(72) Inventor: Tariq Aslam, Wilmslow (GB)

(73) Assignee: CLIN-E-CAL LTD, Cheshire (GB)

( * ) Notice: Subject to any disclaimer, the term of this patent is extended or adjusted under 35 U.S.C. 154(b) by 0 days.

(21) Appl. No.: 15/565,410

(22) PCT Filed: Apr. 11, 2016

(86) PCT No.: PCT/GB2016/051007
§ 371 (c)(1),
(2) Date: Oct. 9, 2017

(87) PCT Pub. No.: WO2016/162699
PCT Pub. Date: Oct. 13, 2016

(65) Prior Publication Data
US 2018/0125392 A1    May 10, 2018

(30) Foreign Application Priority Data
Apr. 9, 2015    (GB) .................................. 1506047.8

(51) Int. Cl.
*A61B 5/097*    (2006.01)
*A61M 15/00*    (2006.01)
(Continued)

(52) U.S. Cl.
CPC ............ *A61B 5/097* (2013.01); *A61B 5/4833* (2013.01); *A61B 5/742* (2013.01); *A61B 5/7405* (2013.01);
(Continued)

(58) Field of Classification Search
CPC ........................................................ A61B 5/097
(Continued)

(56) References Cited

U.S. PATENT DOCUMENTS

| 4,809,692 A | 3/1989 | Nowacki |
| 2013/0151162 A1* | 6/2013 | Harris .................. A61M 15/00 702/19 |
| 2014/0106324 A1* | 4/2014 | Adams ................ A61M 15/009 434/262 |

FOREIGN PATENT DOCUMENTS

| EP | 1407794 A1 | 4/2004 |
| WO | WO2010023591 A2 | 3/2010 |

(Continued)

OTHER PUBLICATIONS

United Kingdom Intellectual Property Office, Search Report for UK App. GB1506047.8, dated Sep. 17, 2015, pp. 1-3, published by United Kingdom Intellectual Property Office Patents Directorate, Newport, South Wales.
(Continued)

*Primary Examiner* — Qutbuddin Ghulamali
(74) *Attorney, Agent, or Firm* — MH2 Technology Law Group, LLP

(57) ABSTRACT

A medicament compliance system, comprising a tonal device associated with an inhaler, the tonal device being arranged to emit a predetermined tone responsive to successful use from the respiratory device. The system also comprises a device comprising a microphone for outputting audio data, a processor, a memory, and a display. The processor is arranged to receive the audio data and to determine whether the audio data corresponds to the predetermined tone, and to display an incentive graphic in response to detection of the predetermined tone.

20 Claims, 4 Drawing Sheets

(51) Int. Cl.
    *A61B 5/00*      (2006.01)
    *A61B 7/00*      (2006.01)
    *A61M 16/06*     (2006.01)
    *A61B 5/087*     (2006.01)

(52) U.S. Cl.
    CPC ........... *A61B 7/003* (2013.01); *A61M 15/009* (2013.01); *A61M 15/0086* (2013.01); *A61B 5/087* (2013.01); *A61M 16/06* (2013.01); *A61M 2205/3375* (2013.01); *A61M 2205/43* (2013.01); *A61M 2205/502* (2013.01)

(58) Field of Classification Search
    USPC ...................................... 340/573.1
    See application file for complete search history.

(56) References Cited

FOREIGN PATENT DOCUMENTS

| | | |
|---|---|---|
| WO | WO2011083377 A1 | 7/2011 |
| WO | WO2013124624 A1 | 8/2013 |
| WO | WO2015006701 A2 | 1/2015 |

OTHER PUBLICATIONS

European Patent Office as ISA, The International Search Report and The Written Opinion, PCT/GB2016/051007, dated May 31, 2016.

\* cited by examiner

INHALER SPACER WITH A MEDICAMENT COMPLIANCE SYSTEM

TECHNICAL FIELD

Embodiments of the invention relate to a medicament compliance system for use with a respiratory device to improve compliance with a medicament dosage regime.

BACKGROUND

Inhaled medicaments are commonly prescribed to patients for treating diseases such as asthma and viral induced wheeze. Inhaled medicaments may be administered via a number of means, including metered dose inhalers ('MDIs'), and nebulisers. MDIs are the most commonly prescribed means for administering inhaled medicaments.

In order to properly use an MDI, a number of coordinated actions are required (pressing down on the inhaler, breathing in deeply as the medication is released, holding your breath and exhaling). Some patients, for example the very young, elderly or disabled, have difficulty completing the required actions in the correct order and at the correct times.

Patients who experience difficulty using an MDI are commonly provided with a spacer device. Spacer devices connect a drug delivery canister (for example, an MDI) to a mask or mouthpiece. Pressing of the drug canister releases the drug into a chamber of the spacer device. The medicament is held within the chamber by a valve, which is opened upon inhalation, allowing the patient to inhale the treatment in his own time through the mask. Cessation of inhalation causes closure of the valve to keep the remaining drug in the chamber of the spacer device.

Use of the spacer device avoids timing issues experienced with MDIs. Indeed, a patient is generally encouraged to breathe "normally" when using a spacer device, rather than to adopt a particular, abnormal, breathing pattern. Further, aerosol is generally issued to the patient from the spacer device more slowly than when issued directly from the MDI, resulting in less of the drug impacting on the back of the mouth and more of the drug reaching the lungs of the patient. Because of this, less medication is needed for an effective dose to reach the lungs, and there are fewer negative side effects, for example from corticosteroid residue in the mouth.

For children, spacer devices are particularly useful, allowing them to gain the benefit of inhaled drugs in a way that they can use at home, without the use of hospital nebulisers and masks. In fact, studies have shown that when used correctly, these devices can match the efficacy of hospital nebulisers in treatment of asthmatic children.

Spacer devices, do however, suffer from a number of problems which can limit their effectiveness. For example, in order to use a spacer device correctly, the patient is required to make an effective seal with the mask. A poor seal will not allow efficient drug delivery. The quality of the seal may be assessed by a parent/supervisor watching a valve of the spacer device to ensure that the valve is moving and by listening for an accompanying sound. The valves, however, are small, such that assessing the quality of the seal this way is often difficult, especially at night.

Further, once a correct seal is made, the patient is required to take multiple separate breaths to inhale the drug. This process may itself need to be repeated multiple times and for severe attacks may need to be performed hourly or two hourly. The difficulty faced by some patients is therefore increased just at the moment when an effective treatment is most in need. For children, such repetition often leads boredom, distraction and an unwillingness to participate, especially when tired or unwell. Furthermore placing a mask over the face of a patient can potentially cause further distress in an already stressful and difficult situation. Such disadvantages can hinder efforts to encourage a patient to adopt their normal breathing pattern, which is required to achieve the most effective administration of the medicament.

It is an object of the present invention to obviate or mitigate one or more of the problems outlined above.

US 2014/0106324 discloses an inhalation training system. However, this system does not assist a patient, particularly children, in monitoring inhalation from a respiratory device, such as an in inhaler.

SUMMARY OF THE INVENTION

According to a first aspect of the invention, there is provided a medicament compliance system comprising a means for generating a predetermined tone associated with a respiratory device, wherein the means for generating a predetermined tone may be arranged to emit the predetermined tone responsive to successful use from the respiratory device and a device comprising a microphone for outputting audio data; a processor; a memory; and a display. In some embodiments, the respiratory device is a respiratory device arranged to administer a medicament. In some embodiments, the respiratory device is an inhaler, wherein successful use comprises successful inhalations of the inhaler. The processor may be arranged to receive the audio data and to determine whether the audio data corresponds to the predetermined tone, and to display an incentive graphic in response to detection of the predetermined tone. The advantage of this is to aid with the compliance of a medicament regime, especially in young of elderly patients where they may find it difficult to inhale the correct dosage and or are easily distracted.

Preferably, the device may be separate from the respiratory device and means for generating the predetermined tone. This enables the patient to be assisted by a helper such as a parent or medical professional, and also enables the device to be placed in the eye line of the patient so they can see what is being shown on the display. The display may be visible by the patient whilst inhaling from the respiratory device, such that the patient may adjust their breathing responsive to the incentive graphic during breathing.

Successful use, which may comprise successful inhalations, are indicative of having at least a predetermined pressure at the means for generating the predetermined tone. This ensures that the tone is only produced when the patient is breathing at the correct rate, thereby encouraging them to breathe normally so as to show the incentive graphic on the display.

The processor may be further configured to receive patient data and to configure the incentive graphic in response to the patient data, enabling the device's content to be customised so the patient can follow a customised dosage regime.

The incentive graphic may be provided as part of a game, wherein the game is configured based upon the patient data, enabling the game's contents to respond to specific characteristics of the patient.

The patient data may be indicative a required number of dose dispensing cycles and the game may be configured to provide a number of levels based upon the required number of dose dispensing cycles. Similarly, where the patient data indicates a required number of inhalations per dose dispensing cycle this may provide a number of stages for each level based upon the number of inhalations. The memory may also comprise a plurality of games and the processor may be configured to select one of said plurality of games based upon the patient data. This allows customisation of the game's contents so as to deliver a personal experience and encourage compliance. Further customisation could be achieved by the received data comprising age data indicative of an age of the patient and wherein the mode of the game may be configured based upon the age of the patient.

The processor may be further configured to show a prompt on said display to incentivise the patient to complete a successful inhalation of the medicament in response to a successful inhalation not being detected by the microphone within a predetermined time period. This enables the device to determine when it is being used and if it is, encourage the patient to breathe normally.

Preferably, the processor may be arranged to continually analyse audio data from the microphone continuously over a predetermined period, in certain embodiments this may be up to 75 ms; optionally the predetermined period may be 25 ms. The audio data may be analysed to detect the predetermined tone produced by the means for generating the predetermined tone, and in some embodiments the audio data may be analysed in a spectral domain, possibly by applying a Fourier transform to the audio data. Analysis of the audio data may result in one or more of a plurality of settings being configured by the processor, wherein one of the settings may relate to a mode based upon a characteristic of the predetermined tone created by the means for generating the predetermined tone. This enables the audio data to be analysed and the device to be configured based upon the characteristics of the patient's breathing. Where there are a plurality of modes, there may be, for example, 3 modes indicative of an increasing difficulty. One mode of operation may be determined by the processor comprising, detecting a peak amplitude in the audio data over a predetermined period; and determining whether said peak amplitude is lower than a maximum of an expected peak range of a base frequency produced by the means for generating the predetermined tone ensuring any sound amplitudes reach a certain expected peak amplitude.

A further mode of operation may be determined by the processor comprising, detecting a peak amplitude in the audio data over a predetermined period; and determining whether said peak amplitude is lower than a maximum of an expected peak range of a base frequency produced by the means for generating the predetermined tone ensuring any sound amplitudes reach a certain expected peak amplitude. Additionally, the processor may determine whether said peak amplitude is lower than a maximum of an expected peak range of a second harmonic frequency produced by the means for generating the predetermined tone. The second harmonic frequency may have a higher frequency than the base frequency; and have a maximum value less than a maximum value of an expected peak range of the second harmonic frequency produced by the means for generating the predetermined tone.

Preferably, an alternative mode of operation may be determined by the processor comprising detecting a peak amplitude in the audio data over a predetermined period; and determining whether said peak amplitude is lower than a maximum of an expected peak range of a base frequency produced by the means for generating the predetermined tone ensuring any sound amplitudes reach a certain expected peak amplitude. Additionally, the process may determine whether said peak amplitude is lower than a maximum of an expected peak range of a second harmonic frequency produced by the means for generating the predetermined tone. The second harmonic frequency may have a higher frequency than the base frequency; and have a maximum value less than the maximum value of the expected peak range of the second harmonic frequency produced by the means for generating the predetermined tone. The second harmonic frequency range may also require the peak amplitude to be higher than a predetermined minimum.

These alternative modes enable the difficulty of the system to be customised based upon the patient's characteristics.

The processor may be arranged to determine the detection of a predetermined tone upon satisfying a plurality of conditions determined by the mode of operation, which may indicate that the patient is inhaling. If it is determined that the patient is already inhaling, by the satisfaction of the conditions in one or more previous periods, the satisfaction of the conditions may not cause a change in the incentive graphic. Alternatively, if it is determined that the patient was exhaling, then the satisfaction of the conditions may indicate the patient has begun to inhale. The start of the start of inhalation may be indicated in the incentive graphic shown on the display. This enables the inhalation by a patient to affect the incentive graphic and therefore act as an encouragement to comply with the medicament regime.

In some embodiments, the processor is arranged to output an indication of a successful breathing cycle. The indication may be output to the display or any other suitable output device. A successful breathing cycle may be determined responsive to detection of one or more of a predetermined pattern of tones at specific frequencies, within specific frequency ranges, and/or durations. Such a breathing cycle may be associated with a pattern of tones produced by each inhale or exhale. The indication of a successful breathing cycle may be output responsive to detection of a predetermined pattern of tones associated with the pattern of breathing. Detection of each tone may be conditional on each tone possessing one or more of a particular frequency, frequency range, or duration. The output of an indication of a successful breathing cycle may further be responsive to a predetermined absence of tones at one or more of a predetermined pattern of frequencies or durations. Determination of a successful breathing cycle may further be responsive to detection of a combination of a pattern of tones and an absence of tones. The output of an indication of a successful breathing cycle may further be responsive to detection of one or more of a predetermined pattern of tones or absence of tones in a particular range of frequencies.

The output of an indication of a successful breathing cycle may be associated with a change in state of the game. Optionally, the indication may be associated with a change in level of the game.

The means for generating the predetermined tone may be a tonal device or a valve opening and closing, enabling the use of the system with or without a tonal device in certain circumstances.

According to a second aspect of the invention, there is provided a computer implemented method for improving compliance with a medicament dosage regime, said regime requiring the inhalation of a predetermined dosage of a medicament using an respiratory device. The method comprise receiving audio data from a microphone; determining whether the received audio data is indicative of a predetermined tone emitted by a means for generating the predetermined tone, associated with the respiratory device, upon successful use of the medicament from the respiratory device; and displaying and updating at least one incentive graphic on a display device in response to the predetermined tone. The advantage of this is to aid with the compliance of a medicament regime, especially in young or elderly patients where they may find it difficult to inhale the correct dosage and or are easily distracted.

Preferably the computer implemented method may include a computer program comprising computer readable instructions that may be configured to cause a computer to carry out a method. Similarly, they may include a computer readable medium which may carry a computer program. This enables the device to store a number of incentive graphics and processes to encourage compliance with the medicament regime.

The computer implemented method may apply a Fourier transform to the received audio data to determine whether the received audio data is indicative of a predetermined tone emitted by the means for generating the predetermined tone. This enables the device to respond to successful use which may be indicative of normal breathing.

The means for generating the predetermined tone may be a tonal device or a valve opening and closing, enabling the use of the method with or without a tonal device in certain circumstances.

According to a third aspect of the invention, there is provided a device to aid with compliance of a medicament regime comprising a microphone for outputting audio data; a processor; a memory; and a display. The processor may be arranged to receive the audio data and to determine whether the audio data corresponds to a predetermined tone produced by a means for generating the predetermined tone, associated with the respiratory device, indicative of successful use of a medicament, and to display an incentive graphic in response to detection of the predetermined tone.

The means for generating the predetermined tone may be a tonal device or a valve opening and closing, enabling the use of the device with or without a tonal device in certain circumstances.

BRIEF DESCRIPTION OF THE DRAWINGS

Embodiments of the invention will now be described by way of example only, with reference to the accompanying figures, in which.

DETAILED DESCRIPTION

Figure 1:
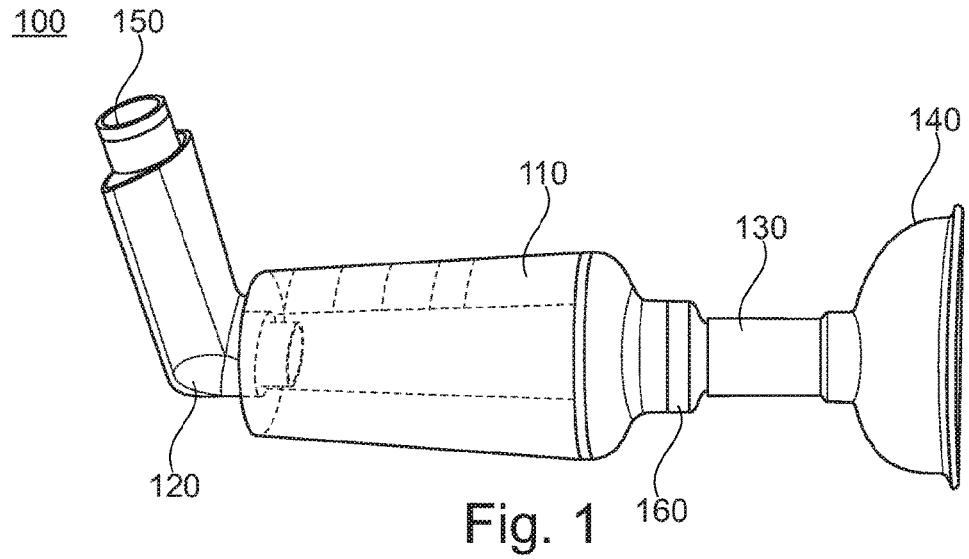
FIG. 1 is an image showing a spacer device attached to a tonal device, medicament dispensing device, and a mask.

Referring to FIG. 1, a spacer device 110 is connected to a respiratory device 120. In some embodiments, the respiratory device 120 is respiratory device arranged to administer a medicament. In some embodiments, the respiratory device 120 is a metered dose inhaler (MDT The spacer device 110 comprises a chamber closed at one end by a tonal device 130 and at the opposing end the MDI 120. Connected to the respiratory device 120, in this embodiment to the tonal device 130, may be a mask 140 to aid in the inhalation of the medicament.

In use, a patient depresses a drug container 150 protruding from the respiratory device 120 releasing a drug contained within the drug container 150. The drug may be released into the spacer device 110 from the drug container 150. The drug is held in the spacer device 110 by a valve 160 located at one of the ends of the spacer device. Upon proper fitment of the mask 140 to the patient's face, inhalation causes the release of the valve 160 allowing a portion of the drug within the spacer device 110 to be inhaled by the patient. Upon inhalation the drug will pass through a means for generating a predetermined tone, in some embodiments this may be a tonal device 130. The tonal device 130 is adapted to produce a desired one or more tones. Alternatively it may be the valve 160, which upon opening and closing emits a sound indicative of a tone. In some embodiments, the means for generating a predetermined tone may be incorporated into the mask 140, the respiratory device 120, or any other suitable aspect of the apparatus. At the end of the inhalation the valve 160 closes such that any remaining drug is held within the spacer device 110. Repeated inhalation/exhalation cycles can be performed until all of the drug contained within the spacer device 110 has been inhaled by the patient.

In certain embodiments, during inhalation, the drug is forced through the tonal device 130 by a pressure differential caused by the patient inhaling. Upon passing through the tonal device 130, the tonal device 130 emits one or more predetermined tones dependent upon the features of the patient's inhalation. Should the inhalation meet predetermined criteria a predetermined tone is emitted by the tonal device 130. The predetermined criteria may be selected to ensure proper administration of the drug to the patient.

The one or more predetermined tones may be detected by a microphone contained within or attached to a computing device 200. In some embodiments, the tone may not be detectable by the human ear. The computing device 200 may be a mobile telephone, tablet computer, laptop computer or desktop computer, or any other suitable device. In some embodiments the computing device 200 is supported, in use, by the respiratory device 120. The computing device 200 can be used to display an incentive graphic to the user to encourage compliance with a medication regime. For example, an interactive game, adapted to encourage a patient to inhale the required number of breaths may be displayed on a screen of the computing device 200. The screen of the computing device may be visible to the patient whilst breathing through the respiratory device 120. In more detail, games operating on the computing device 200 are configured by the inhalation of the patient and in response to the predetermined tone produced by the tonal device 130. The detection of the predetermined tone enables a patient to manipulate aspects of the games in a way which will keep the patient motivated and entertained throughout the proposed period of treatment, and will encourage the patient to adopt a normal breathing pattern by ensuring there is a full seal between the patient's mouth and the system 100, be it made directly with the tonal device 130 or with the use of a mask 140. The computing device 200 can thus be also viewed as an entertainment device.

Figure 2:
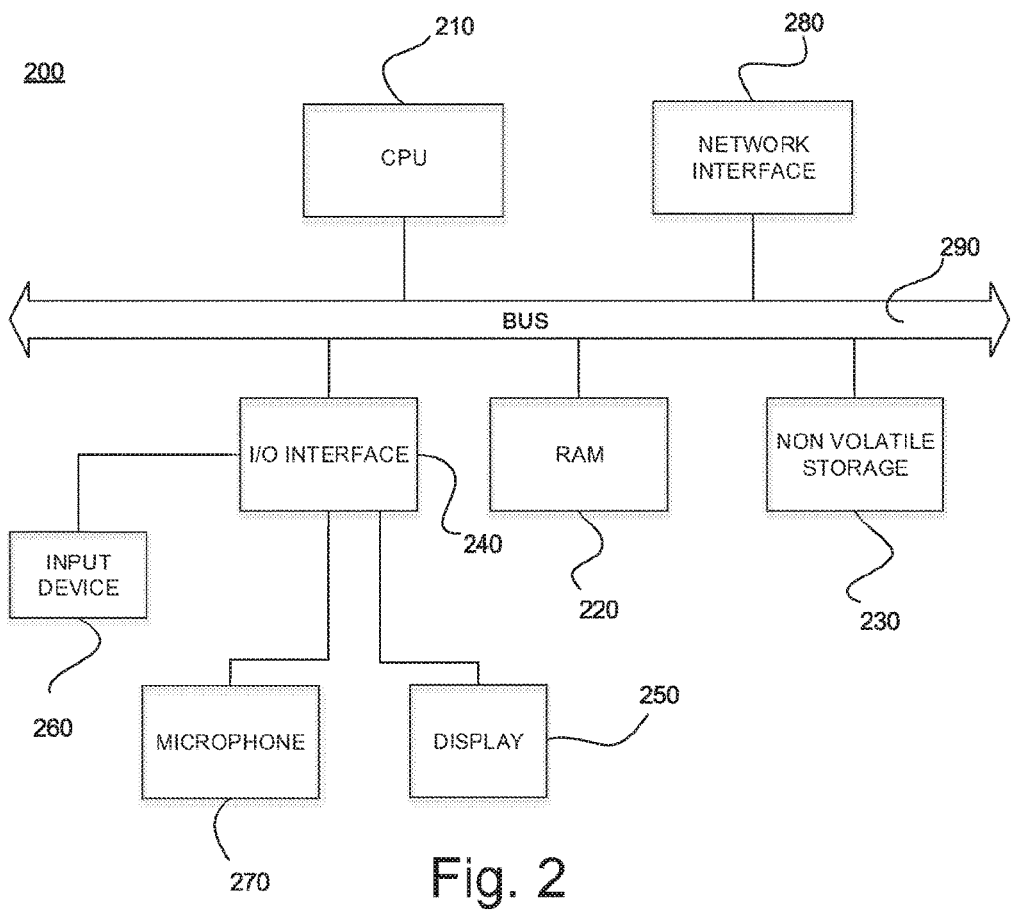
FIG. 2 is a schematic illustration of example components of the computing device used to detect a tone and display an incentive graphic.

An example of components of the computing device 200, which can be used to implement embodiments of the present invention, is now described with reference to FIG. 2. It will be appreciated that the components of the computing device 200 in FIG. 2 are merely exemplary, and that any suitable computing device may be used to implement the embodiments of the present invention. The computing device 200 comprises a CPU 210 which is configured to read and execute instructions stored in volatile memory 220 which may take the form of random access memory. The volatile memory 220 stores instructions for execution by the CPU 210 and data used by those instructions. In the present embodiment, the instructions stored in the volatile memory 220 are instructions to cause the CPU 210 to run an application providing interactive games designed to encourage a patient to properly inhale a required amount of drug.

The computing device 200 further comprises non-volatile memory 230. The non-volatile memory 230 may take any appropriate form, such as a solid state drive ('SSD'), or hard disk drive ('HDD'). The computing device 200 further comprises an I/O interface 240 to which are connected input and output devices used in connection with the computing device 200. A display 250 shows the visual outputs of the interactive game during use. Input devices connected to the I/O interface 240 may include physical keys 260 which allow user interaction with the computing device 200. Alternatively or additionally, the display 250 may provide a touchscreen allowing a patient or supervisor to interact with the user interface displayed on the touchscreen. A microphone 270 is connected to the I/O interface 240 allowing sound input to be provided to the computing device 200. In particular, the microphone 270 allows for the predetermined tone from the tonal device 130 to be detected by the computing device 200 for processing by the application. A network interface 280 allows the computing device 200 to be connected to an appropriate computer network so as to receive and transmit data from and to other computing devices. In this way, the computing device 200 may receive updates (for example, new games), or receive/transmit patient details/progress (for example, readings from use of the device) from/to another device (such as one belonging to a clinician). The CPU 210, volatile memory 220, non-volatile memory 230, I/O interface 240, and network interface 280 are connected together via a bus 290.

As described above, the computing device 200 runs an application configured to detect signals from the microphone 270 indicative of the predetermined tone produced by the tonal device 130. The detected predetermined tone and its characteristics are used as an input for the games which can be played by the patient. Each game is represented on the display 250, which in certain embodiments may be placed in the patient's line of sight.

Games are created so as to respond to the tone generated by the tonal device 130 or by the valve 160 opening and closing as a result of the breathing action associated with inhalation. The characteristics of the tone are recorded as audio data by the computing device 200 and analysed by applying a Fourier transform the audio data. Upon application of the Fourier transform, the analysis results in a number of peaks representing the frequencies of the sound recorded in the audio data. Comparisons are then made to determine whether any of the peak frequencies in the audio data correspond with frequencies which would be expected to be created by the tonal device 130. When a tone is detected, the game responds by displaying an action indicative of inhalation on the display 250 of the computing device. An example of such game is where detection of the inhalation and then subsequent exhalation causes a bubble, shown on the display 250 to inflate and float away.

The tonal device 130 and the mask 140 may be configured in such a way that the predetermined tone is only generated when the tonal device detects a pressure differential indicative that a proper seal is made with the mask 140. In this way, the patient is required to maintain a proper seal with the mask 140 to operate the game.

Unintentional failure to manipulate the game objects shown on the display 250 therefore acts as an indication of incorrect usage of the system 100, and can provide motivation to encourage correct use.

Figure 3:
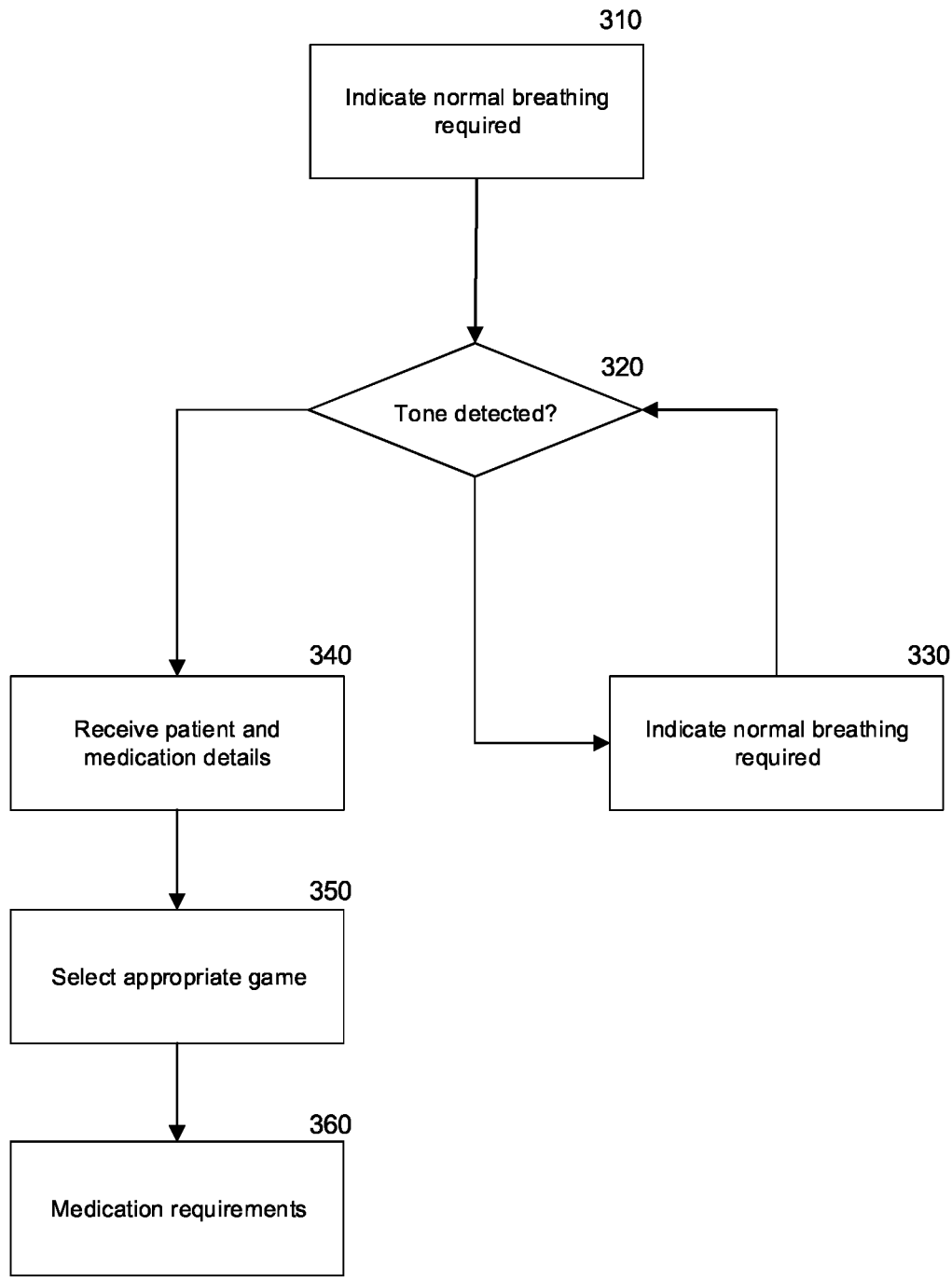
FIG. 3 is a flowchart showing the initialisation process carried out by the computing device in accordance with an embodiment of the present invention.

Upon starting the application a start-up process is performed by the computing device 200 which will be described with reference to FIG. 3. At step 310 the application shows a prompt on the display 250 indication to the patient that they should breathe normally into the mask. At this stage, a parent or supervisor may be required to ensure that correct breathing is maintained and that a proper seal has been made with the mask 140. At step 320 the application determines whether the predetermined tone produced by the tonal device 130 as a result of the patient breathing normally, has been detected. If it is determined that the predetermined tone is not detected at the microphone (according to the methods described below), processing passes to step 330 at which a prompt is shown on the display 250 indicating for the patient to breathe normally to enable the tonal device 130 to produce the predetermined tone. Processing then passes back to step 320 and continues to loop between steps 320 and 330 until the predetermined tone is detected by the microphone 270.

If the predetermined tone is detected by the microphone 270, processing passes to step 340 at which the display 250 shows a prompt for the patient or the supervisor to input the patient's age and how many depressions of the drug container 150 are required. In general, each depression of the drug container 150 requires a predetermined number inhalations/exhalations by the patient, although it will be appreciated that this may vary in dependence upon a number of factors including, for example, the size of the inhaler spacer 110. Upon receiving the patient and dosage details, processing passes to step 350 at which the details are used to select and configure an appropriate game. Where a patient requires a predetermined number of cycles of a predetermined number of inhalations, a selected game may be configured to provide a number of levels indicative of the number of cycles, each level comprising a number of stages indicative of the number of inhalations before completion of that level. A difficulty level of the game may be selected based upon an age of the patient, the possible difficulty levels are details further below.

As mentioned above, in certain embodiments it may be desirable to provide different levels of difficulty to be selected by the patient and/or supervisor in order to provide maximum encouragement and compliance with the medicament regime. In a first mode of operation the computing device 200 may be configured to detect a sound wherein the peak amplitude is in the range outside that emitted by the tonal device 130. Said peak amplitude should also be significantly lower than the maximum expected peak range of the base frequency of the tonal device 130. In addition, in the expected peak range of the base frequency, any of the sound amplitudes should reach a certain expected peak amplitude.

When configured to operate in a second mode, the above conditions used for the first mode apply, but they relate not only to the base frequency, but also to a second harmonic frequency of the tone generated by the tonal device 130. The second harmonic frequency is a higher frequency of sound than the base frequency. In this situation a measurement taken prior to the second harmonic must have a maximum value far less than the maximum value of the expected peak range.

When configured to operate at third mode, the above conditions used for the second mode apply, with the added condition that the second harmonic frequency range of any amplitude of tone generated by the tonal device 130 must exceed a certain minimum. In a preferred embodiment the expert difficulty mode may be selected as the default mode of operation to encourage maximum compliance and correct breathing when using the system 100.

Should the tone generated by the tonal device 130 and detected by the microphone 270 satisfy the conditions of the difficulty setting selected, the CPU 210 indicates that a tone has been detected by the microphone 270 and processes the signal in accordance with the steps detailed below.

Figure 4:
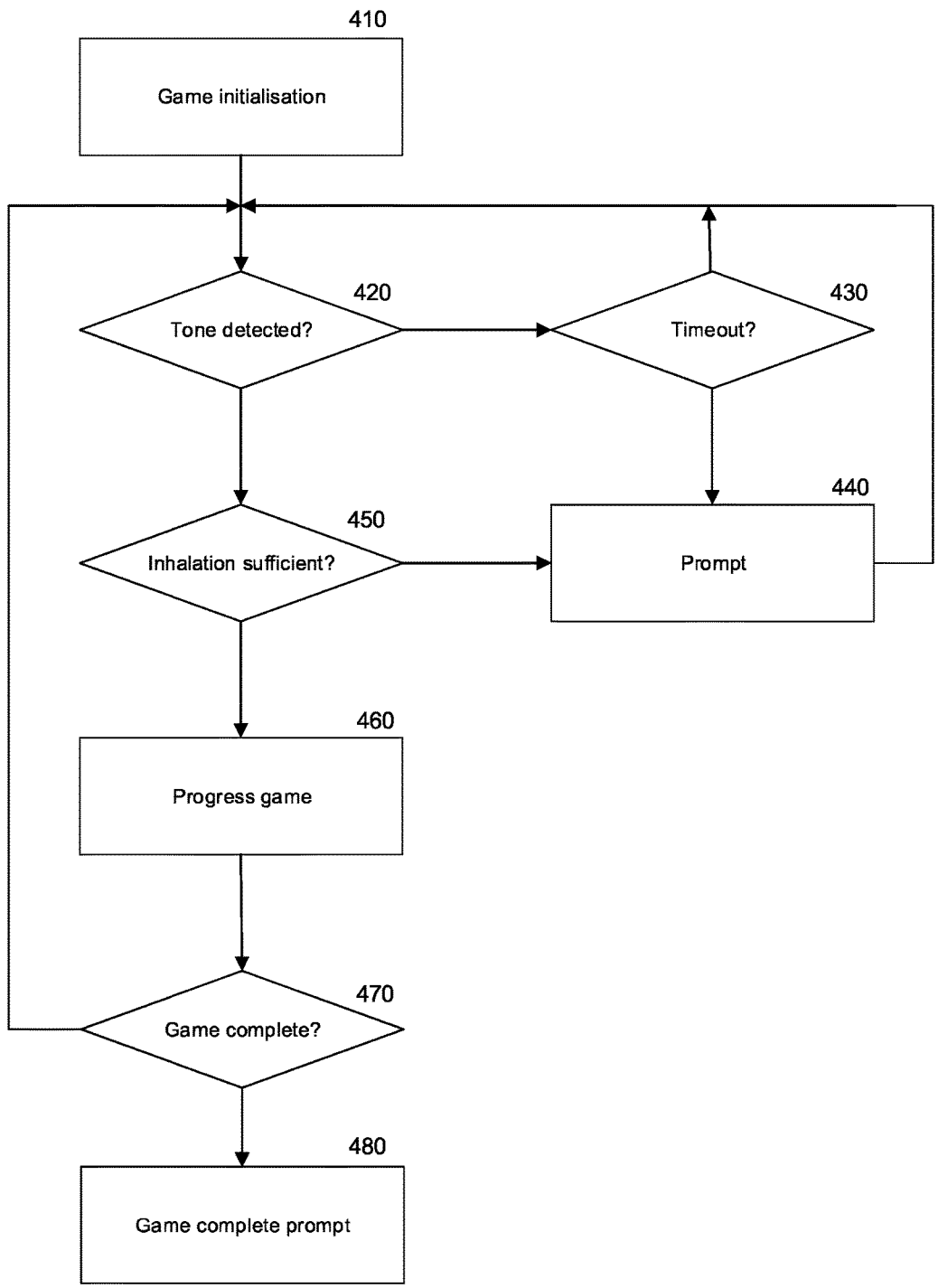
FIG. 4 is a flowchart showing processing carried out by the computing device to display a game to a patient in accordance with an embodiment of the present invention.

Processing carried out by the computing device 200 to present a game is now described with reference to FIG. 4. At step 410, the game selected at step 350 of FIG. 3 is initialised. Processing passes to step 420 at which it is determined whether the predetermined tone, from the tonal device 130 or the valve 160 opening and closing, has been detected by the microphone 270. If the predetermined tone has not been detected, processing passes to step 430 at which it is determined whether a timeout condition has occurred. If at step 430 it is determined that a timeout condition has not occurred then processing passes back to step 420. However, if it is determined that a timeout condition has occurred, processing passes to step 440 at which a motivational prompt is shown on the display 250 to encourage the patient or supervisor to ensure the system 100 is being used correctly. For example, a prompt may be displayed to request that the supervisor ensure that a correct seal has been made with the mask 140. Processing passes from step 440 back to step 420.

If at step 420, the predetermined tone is detected by the microphone 270, processing passes to step 450, at which it is determined whether the detected tone is sufficient (based upon the difficulty criteria discussed above) to indicate correct usage of the system 100. If at step 450, it is determined that the detected tone is not sufficient processing passes to step 440, and loops between steps 420, 430, 440, and 450 until a sufficient tone is detected by the microphone 270. Upon detection of a sufficient tone processing passes to step 460 at which the patient's progress in the game is updated to indicate a successful inhalation/exhalation. The updated progress in the game causes a corresponding update to the game graphics shown on the display 250 to display the patient's progress and motivate further progress.

The game may display an indication of an end point of the game and therefore their progress towards inhaling the required dosage. Once the progress is update processing continues to step 470 at which it is determined whether the patient has completed the game. If the game has been completed processing continues to step 480 where the patient is informed that the game, and therefore the dosage regime, has been successfully completed. If the game is not finished then processing returns to step 420 and waits to detect a further tone indicating a subsequent inhalation.

As described with reference to FIG. 4, a patient's progress in the game is updated in response to detection of successful inhalation/exhalation. In some embodiments of the present invention, when a tone is detected which is not sufficient to indicate a complete inhalation/exhalation there may also be an effect produced on the display 250 to encourage more persistent/greater strength of inhalation. For example in a game to blow out the candles on a cake (where the candle being blown out indicates a fully successful inhalation/exhalation), candles may be caused to flicker in response to a tone indicative of an inhalation/exhalation which was not sufficiently strong. A further example may be in a game to blow bubbles, a bubble may be shown to partially inflate, but to subsequently deflate.

In some embodiments, the computing device 200 may be configured to output an indication of a successful breathing cycle. The indication may be output to the display 250, or any other suitable output device. A successful breathing cycle may be determined responsive to detection of one or more of a predetermined pattern of tones at specific frequencies, within one or more frequency bands, and/or durations. Detection of each tone may be conditional on each tone possessing one or more of a particular frequency, being within a frequency band, and/or duration.

Figure 5:
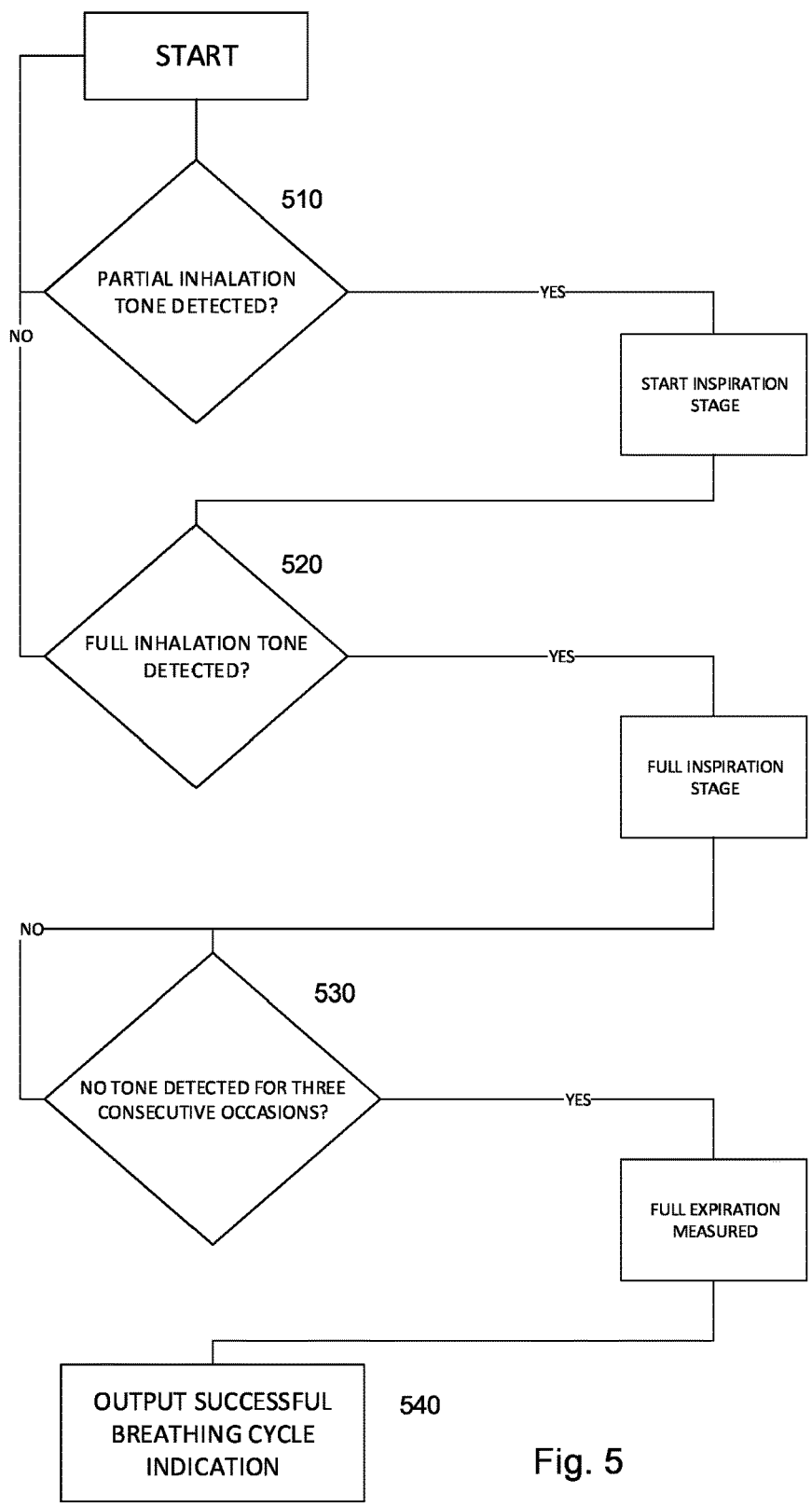
FIG. 5 is a flowchart showing a breathing cycle detection process in accordance with an embodiment of the present invention.

FIG. 5, for example, shows a tone detection pattern representing a successful breathing cycle. At 510, the computing device 200 is configured to detect a partial inhalation tone generated from the tonal device 130 via the microphone 270. If a good, i.e. meeting one or more predetermined criterial, partial inhalation tone is detected, the computing device 200 is then configured to listen for (determine) a full inhalation tone 520. On sequential detection of a full inhalation tone, the computing device 200 is then configured to listen for a predetermined period of silence, or an absence of tones within a specific frequency range or within a specific frequency band. In some embodiments, silence may comprise a tone of a lower volume than a predetermined threshold. If a further inhalation tone is detected, this represents excessive inspiration, and the breathing cycle does not progress. If absence of the tone is measured for the predetermined period of time, full expiration is measured, and a successful breathing cycle can be determined to have occurred. In this case, the computing device 200 is further configured to listen for a predetermined absence of tones at one or more of a predetermined pattern of frequencies and durations, representing the end of inhalation or exhalation. In some embodiments, the computing device 200 will be configured to detect a tone or an absence of a tone in a particular frequency range or band. In some embodiments, the successful breathing cycle will have been determined to have occurred upon detection of a combination of successful inhalations and exhalations.

The output of an indication of a successful breathing cycle may be associated with a change in state of the game, or a change in graphics. Optionally, the indication may be associated with a change in level of the game.

Similarly, unsuccessful breathing cycles may be indicated to the display 250 in a similar fashion. The computing device 200 may be configured to output an indication of a failure to complete a successful breathing cycle to the display 250. Thus, real-time visual feedback of the inhalation and expiration cycle may be output to the user. In some embodiments the computing device 200 may be adapted to provide an alarm to remind the patient to use their respiratory device at predetermined times.

While the above description has been concerned with the display of electronic 'games' to a patient, it will be appreciated that any content may be shown on the display 250 which is suitable for motivating a user to complete a required number of inhalations of a drug. For example a moving scene may be displayed, wherein the patient must complete regular, successful inhalations/exhalations in order to maintain the movement of the scene. Alternatively, the content may comprise a cartoon character as part of a continuous storyline, wherein detection of a successful breathing pattern further advances movement of the cartoon character, or further advances the storyline. Detection of tones that do not constitute the successful breathing pattern (i.e. excess inhalations or exhalations) similarly inhibit movement of the scene, and thus prevent game progress. In this way, the flow of movement seen on the display 250 correlates with the pattern of breathing.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A medicament compliance system, comprising:
  a tonal device for generating a predetermined tone associated with a respiratory device, the tonal device being arranged to emit the predetermined tone responsive to successful inhalations from the respiratory device;
  a device comprising:
    a microphone for outputting audio data;
    a processor;
    a memory; and
    a display;
    wherein the processor is arranged to:
      receive the audio data;
      determine whether the audio data corresponds to the predetermined tone, wherein the determining whether the audio data corresponds to the predetermined tone comprises the processor:
        determining a peak amplitude of a sound outside of a predetermined harmonic frequency range emitted by the tonal device; and
        determining whether, in an expected peak range of a harmonic frequency of the tonal device, a sound amplitude reaches an expected peak amplitude;
      and display an incentive graphic in response to detection of the predetermined tone.

2. The medicament compliance system according to claim 1, wherein the medicament compliance system is a respiratory device arranged to administer a medicament.

3. The medicament compliance system according to claim 1, wherein the medicament compliance system is remote from the respiratory device and the tonal device.

4. The medicament compliance system according to claim 1, wherein the display is visible to the user while inhaling.

5. The medicament compliance system according to claim 1, wherein the processor is arranged to analyze the audio data by applying a Fourier transform to the audio data.

6. The medicament compliance system according to claim 1, wherein analysis of the audio data results in one or more of a plurality of settings being configured by the processor, wherein at least one of the settings defines a mode of operation.

7. The medicament compliance system according to claim 6, wherein the mode of operation is determined by the processor comprising:
  detecting a peak amplitude in the audio data over a predetermined period; and
  determining whether said peak amplitude is lower than a maximum of an expected peak range of a base frequency produced by the tonal device ensuring any sound amplitudes reach a certain expected peak amplitude.

8. The medicament compliance system according to claim 6, wherein the mode of operation is determined by the processor comprising:
  detecting a peak amplitude in the audio data over a predetermined period;
  determining whether said peak amplitude is lower than a maximum of an expected peak range of a base frequency produced by the tonal device ensuring any sound amplitudes reach a certain expected peak amplitude;
  determining whether said peak amplitude is lower than a maximum of an expected peak range of a second harmonic frequency produced by the tonal device;
  the second harmonic frequency having a higher frequency than the base frequency; and
  the second harmonic frequency having a maximum value less than a maximum value of an expected peak range of the second harmonic frequency produced by the tonal device.

9. The medicament compliance system according to claim 6, wherein the mode of operation is determined by the processor comprising:
  detecting a peak amplitude in the audio data over a predetermined period;
  determining whether said peak amplitude is lower than a maximum of an expected peak range of a base frequency produced by the tonal device ensuring any sound amplitudes reach a certain expected peak amplitude;

determining whether said peak amplitude is lower than a maximum of an expected peak range of the second harmonic frequency produced by the tonal device;

the second harmonic frequency having a higher frequency than the base frequency;

the second harmonic frequency having a maximum value less than the maximum value of the expected peak range of the second harmonic frequency produced by the tonal device; and a range of the second harmonic frequency requires the peak amplitude to be higher than a predetermined minimum.

10. The medicament compliance system according to claim 1 wherein the indication of successful inhalations comprises having at least a predetermined pressure at the tonal device.

11. The medicament compliance system according to claim 1 wherein said processor is further configured to receive patient data and to configure the incentive graphic in response to the patient data.

12. The medicament compliance system according to claim 11, wherein the incentive graphic is provided as part of a game, and wherein the game is configured based upon the patient data.

13. The medicament compliance system according to claim 11, wherein the patient data is indicative of a required number of dose dispensing cycles and a required number of inhalations per dose dispensing cycle and the game is configured to provide a number of levels based upon the required number of dose dispensing cycles and a number of stages for each level based upon the required number of inhalations.

14. The medicament compliance system according to claim 1, wherein the processor is further configured to show a prompt on the display to incentivize a patient to complete a successful inhalation of the medicament in response to a successful inhalation not being detected by the microphone within a predetermined time period.

15. The medicament compliance system according claim 1, wherein the tonal device comprises a valve that is configured to open and close.

16. A computer implemented method for improving compliance with a medicament dosage regime, said regime requiring the inhalation of a predetermined dosage of a medicament using a respiratory device, the method comprising:

receiving audio data from a microphone;

determining whether the received audio data is indicative of a predetermined tone emitted by a tonal device, associated with the respiratory device, upon successful inhalation of the medicament from the respiratory device, wherein the determining whether the audio data is indicative of the predetermined tone comprises determining a peak amplitude of a sound outside of a predetermined harmonic frequency range emitted by the tonal device; and determining whether, in an expected peak range of a harmonic frequency of the tonal device, a sound amplitude reaches an expected peak amplitude; and displaying and updating at least one incentive graphic on a display device in response to the predetermined tone.

17. The computer implemented method for improving compliance with a medicament dosage regime according to claim 16, wherein the respiratory device is arranged to administer the medicament.

18. The computer implemented method according to claim 16, wherein a Fourier transform is applied to the received audio data to determine whether the received audio data is indicative of the predetermined tone emitted by the tonal device.

19. The computer implemented method according to claim 16, wherein the tonal device comprises a valve that is configured to open and close.

20. The computer program comprising computer readable instructions configured to cause a computer to carry out a method according to claim 16 and a non-transitory computer readable medium carrying the computer program.

\* \* \* \* \*